(12) United States Patent  
Hoagland

(10) Patent No.: US 6,895,805 B2  
(45) Date of Patent: May 24, 2005

(54) HYDROGEN GAS INDICATOR SYSTEM

(76) Inventor: William Hoagland, 7253 Siena Way, Boulder, CO (US) 80301

( * ) Notice: Subject to any disclaimer, the term of this patent is extended or adjusted under 35 U.S.C. 154(b) by 0 days.

(21) Appl. No.: 10/450,007

(22) PCT Filed: Dec. 5, 2001

(86) PCT No.: PCT/US01/47151

§ 371 (c)(1),
(2), (4) Date: Jun. 5, 2003

(87) PCT Pub. No.: WO02/46740

PCT Pub. Date: Jun. 13, 2002

(65) Prior Publication Data

US 2004/0050143 A1 Mar. 18, 2004

Related U.S. Application Data

(60) Provisional application No. 60/251,297, filed on Dec. 5, 2000.

(51) Int. Cl.$^7$ .............................................. G01N 7/00
(52) U.S. Cl. .................... 73/31.06; 73/31.05; 422/56; 422/58
(58) Field of Search ........................ 73/31.05, 31.06; 422/56.58, 56, 58

(56) References Cited

U.S. PATENT DOCUMENTS

| | | |
|---|---|---|
| 2,249,867 A | 7/1941 | Snelling |
| 3,472,629 A | 10/1969 | Rommel et al. |
| 4,078,893 A | 3/1978 | Gilman et al. |
| 4,271,121 A | 6/1981 | Diller et al. |
| 4,340,885 A | 7/1982 | Chavis et al. |
| 4,347,732 A | 9/1982 | Leary |
| 4,443,791 A | 4/1984 | Risgin |
| 4,892,834 A | 1/1990 | Rauh |
| 4,900,405 A | 2/1990 | Otagawa et al. |
| 5,447,688 A | 9/1995 | Moore |
| 6,277,589 B1 | 8/2001 | Seibert et al. |
| 6,513,362 B1 * | 2/2003 | Yadav et al. ............... 73/31.05 |
| 6,691,554 B2 * | 2/2004 | Eastman et al. ........... 73/25.03 |

* cited by examiner

Primary Examiner—Michael Cygan
(74) Attorney, Agent, or Firm—Santangelo Law Offices, P.C.

(57) ABSTRACT

A hydrogen gas indicator system that provides various substrate materials (4) that support hydrogen gas sensor (1) materials with discrete indicia (7) that provide information separate from any change in the physical properties of the hydrogen gas sensor itself.

33 Claims, 6 Drawing Sheets

B

A

HYDROGEN GAS INDICATOR SYSTEM

This application is the United States National Stage of International Application No. PCT/US01/47151, filed Dec. 5, 2001, which claims the benefit of U.S. Provisional Patent Application No. 60/251,297, filed Dec. 5, 2000, each hereby incorporated by reference herein.

This application claims the benefit of U.S. Provisional Patent Application No. 60/251,297, filed Dec. 5, 2000, hereby incorporated by reference.

I. TECHNICAL FIELD

A hydrogen gas indicator system that provides indicators of the presence of hydrogen gas in the environment that are discrete from the hydrogen gas sensor material itself.

II. BACKGROUND

In the coming decades, hydrogen may be stored and used in new energy systems in vast quantities. Advances in fuel cells and advances to electric vehicles have brought hydrogen gas to the forefront of the various energy candidates to meet our future energy demands. However, there remains a general perception about the safety with respect to the widespread use of hydrogen gas as a fuel.

Concerns about hydrogen safety could be a longstanding and formidable barrier to its early introduction as a fuel in clean, sustainable energy systems. Such safety concerns are particularly difficult to overcome where there is limited operating experience and few, if any, published codes and standards. This negative perception affects consumer acceptance, production liability, insurability, permitting requirements, and the establishment of other ordinances and regulations, all of which are required for the widespread introduction of commercial hydrogen gas fuels, products, or systems into the marketplace.

Prominent among these concerns may be the possibility of a fire or explosion resulting from an undetected hydrogen gas leak. Current technology for detecting the presence of free hydrogen in a mixture of other gases has improved, and there exist various regulations requiring the use of hydrogen detection devices to detect the presence of hydrogen gas at 1 volume percent where gaseous hydrogen buildup is possible (29 C.F.R. 1910.106 (1996), hereby incorporated by reference) and at 0.4 volume percent for confined spaces (29 C.F.R. 191.146 (1996), hereby incorporated by reference). Simple, cost effective means for hydrogen gas detection and indication of information to persons about the level of hydrogen gas present in various environments in which hydrogen gas can be used or may accumulate has been given little, if any, attention and significant problems remain, yet to be resolved.

A significant problem with existing hydrogen gas sensor technology can be that it may be too large, too immobile, too complex, or too expensive to introduce into a mass market as a personal hydrogen gas detection or indicator technology. Mass spectrometers and chromatographs, for example, are extremely sensitive, but are also large, immobile, expensive, require skilled operators, and may have long response times.

Another significant problem with existing hydrogen gas sensor technology can be that it is not practical for continuous monitoring. Leak detection by observing the formation of bubbles in a liquid material, for example, can be one of the simplest manners of leak detection but only has practical use in the detection of inert gases that are at low pressure and when the temperatures is above freezing.

Another significant problem with existing hydrogen gas sensor technology can be that the hydrogen sensor can be dangerous to use. For example, glow plug technology ignites combustible gas and the heat of combustion is then measured. As can be understood, an ignition source can be dangerous when there is a large amount of the combustible material available.

Another significant problem with existing hydrogen gas sensor technology can be that the technology lacks specificity to hydrogen gas. For example, catalytic combustion sensors can detect hydrogen gas by sensing the heat generated by the combustion of hydrogen with oxygen on the surface of a catalyst such as palladium or platinum. However, catalytic sensors also combust other gases such as methane as well and may provide false indications of the presence of hydrogen gas. Ultrasonic leak detectors are not specific to hydrogen gas and cannot differentiate combustible mixtures from non-combustible mixtures of gases.

Another significant problem with existing hydrogen gas sensor technology can be that the technology does not work in certain environments. Catalytic combustion sensors may not work in atmospheres of inert gas or pure hydrogen and semiconducting oxides may not work in atmospheres of inert gas. Bubble detection, electrochemical sensors using selectably permeable membranes, or thermal conductivity sensors may not work or may work inconsistently at lower or variable temperatures.

Another significant problem with existing hydrogen gas sensor technology can be that the technology may not provide discrete indicia beyond the change in the physical or electrical properties of the hydrogen gas sensor itself that can be visually, audibly or tactily discerned or observed by persons in the environment surrounding the hydrogen gas sensor.

The instant invention addresses each of the above-mentioned problems in a practical manner.

III. DISCLOSURE OF THE INVENTION

Accordingly, a broad object of the invention can be to provide a hydrogen gas indicator that detects hydrogen gas and provides discrete indicia of the presence of hydrogen gas to person in proximity to the hydrogen gas indicator.

Another broad object of embodiments of the invention can be to provide a hydrogen gas indicator that is reliable when used in atmospheres of inert gas, hydrogen gas, or mixtures of gases; or in environments that have variable temperature including high temperatures such as above about 100° Centigrade and low temperatures such as below 0° Centigrade.

Another broad object of embodiments of the invention can be to provide a hydrogen gas indictor that can be mass marketed as a personal hydrogen gas indicator that is simple, low cost, or portable and does not require any special expertise to use.

Another broad object of embodiments of the invention can be to provide friable or particulate substrates that can be entrained in liquids or contained in gas sampling devices.

Another broad object of embodiments of the invention can be to provide substrate materials that are separable or peelable from a disposable substrate material.

Another broad object of embodiments of the invention can be to provide material substrate containment elements so that the various embodiments of hydrogen gas sensors can be applied to or used with outwear.

Another broad object of the invention can be to provide discrete indicia operably responsive to the hydrogen gas sensor that can provide information separate from any change in the physical or electrical properties of the hydrogen gas sensor itself.

Naturally further objects of the invention are disclosed throughout other areas of specification.

IV. BRIEF DESCRIPTION OF THE DRAWINGS

V. MODE(S) FOR CARRYING OUT THE INVENTION

The invention involves devices, methods, and compositions involving hydrogen gas sensors that can provide discrete indicia of the presence of hydrogen gas separate from any change in the physical properties of the hydrogen gas sensor material itself.

Figure 1:
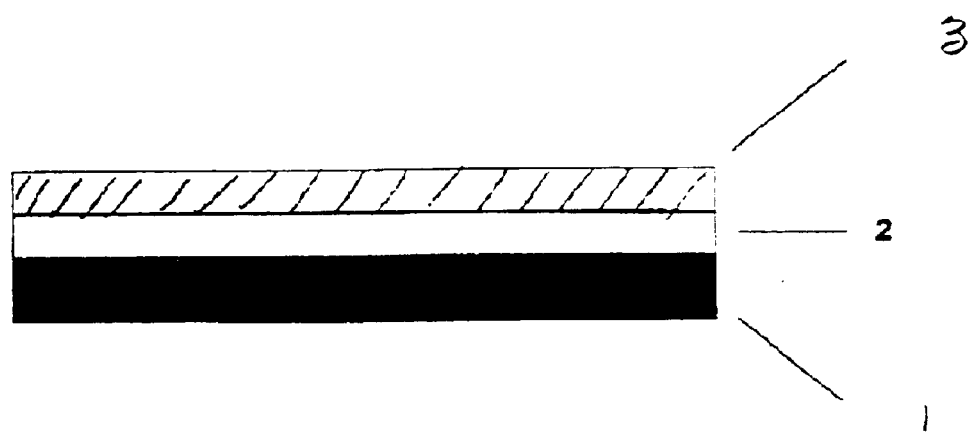
FIG. 1 shows an embodiment of a hydrogen gas sensor having a hydrogen gas sensor material, a catalyst material, and a molecular diffusion barrier selectably permeable to hydrogen gas.

Now referring primarily to FIG. 1, certain embodiments of the invention can comprise a hydrogen gas indicator comprising three components. The first component can be a hydrogen gas sensor material (1) of transition metal oxides or oxysalt such as vanadium oxide, tungsten oxide, molybdenum oxide, yttrium oxide, or combinations thereof, as examples. When exposed to atomic hydrogen the metal oxide can be reduced to the corresponding metal. The reduction from the metal oxide to the corresponding metal can be accompanied by a change in electrical conduction, electrical resistivity, electrocapacitance, magneto-resistance, photoconductivity, or optical properties of the hydrogen gas sensor (1). The change in such physical properties can be reversed by removing the transitional metal from exposure to hydrogen gas and by exposing it to oxygen or the partial pressure of oxygen available in a mixture of gases, thereby converting the transitional metal(s) back to the corresponding metal oxide. In some embodiments of the invention the hydrogen gas sensor (1) material, a chemochromic transition metal can be used such as tungsten oxide that becomes noticeably darker in color upon conversion from tungsten oxide to tungsten metal (the color change being reversible upon exposing the tungsten metal to oxygen), as an example. In other embodiments of the invention, the hydrogen gas sensor can be part of a circuit that can carry a signal. The output of the signal can be indicative of the presence or absence of hydrogen in the environment. In certain embodiments of the invention, the hydrogen gas sensor can comprise a thin film having a thickness of between about 0.2 microns to about 10 microns in thickness. The transition metal thin film can be formed by vacuum vapor distillation, sputtering, electrophoretic, or other methods of metal deposition. The hydrogen gas sensor usefully employed in the practice of the invention may be of a form as more fully described in the following references: U.S. Pat. No. 5,356,756 issued Oct. 18, 1994 to R. Cavicchi et al.; U.S. Pat. No. 5,345,213 issued Sep. 6, 1994 in the names of S. Semancik, et al; J. S. Suehle, R. E. Cavicchi, M. Gaitan, and S. Semancik, "Tin Oxide Gas Sensor fabricated using CMOS Micro-hotplates and In Situ Processing," IEEE Electron Device Lett. 14, 118–120 (1993); S. Semancik and R. E. Cavicchi, "The use of surface and thin film science in the development of advanced gas sensors," Appl. Surf. Sci 70/71, 337–346 (1993); R. E. Cavicchi, J. S. Suehle, K. G. Kreider, M. Gaitan, and P. Chaparala, "Fast Temperature Programmed Sensing for Microhotplate Gas Sensors," IEEE Electron Device Letters 16, 286–288 (1995); R. E. Cavicchi, J. S. Suehle, K. G. Kreider, B. L. Shomaker, J. A. Small, M. Gaitan, and P. Chaparala, "Growth of $SnO_2$ films on micromachined hotplates," Appl. Phys. Lett. 66 (7), 812–814 (1995); C. L. Johnson, J. W. Schwank, and K. D. Wise, "Integrated Ultra-thin film gas sensors," Sensors and Act B 20, 55–62 (1994); X. Wang, W. P. Carey, and S. S. Yee, "Monolithic thin film metal oxide gas sensor arrays with application to monitoring of organic vapors," Sensors and Actuators B 28, 63–70 (1995); N. R. Swart and A. Nathan, "Design Optimization of integrated microhotplates," Sensors and Act A 43, 3–10 (1994); and N. Najafi, K. D. Wise, and J. W. Schwank, "A micromachined thin film gas sensor," IEEE Electron Device Lett. 41 (10) (1994). The disclosures of such references are hereby incorporated herein by reference in their entireties, as is the disclosure of "F. DiMeo Jr., S. Semancik, R. E. Cavicchi et al., "MOCVD of $SnO_2$ on silicon microhotplate arrays for use in gas sensing application," Mater. Res. Soc. Symp. Proc. 415, 231–6 (1996), each hereby incorporated by reference.

Again referring primarily to FIG. 1, the second component of the hydrogen gas indicator invention can comprise a catalyst material (2) that facilitates the conversion of molecular hydrogen gas to atomic hydrogen gas. With respect to some embodiments of the invention the catalyst material (2) can be selected from the group of platinum, palladium, rhodium, nickel, combinations of these metals, or alloys of these materials with other metals such as copper, cobalt, iridium, magnesium, calcium, barium, strontium, or the like. The catalyst material can be applied directly to the hydrogen gas sensor by as described above and can have thickness of between about 0.5 microns to about 10 microns with respect to some embodiments of the invention.

A third component of the hydrogen gas indicator invention can further comprise a molecular diffusion barrier (3) that allows selectively permeable diffusion of molecular hydrogen gas or atomic hydrogen gas. The molecular diffusion barrier (3) should be continuous and atomically dense in order to provide an effective barrier against oxidation of the transition metal of the hydrogen gas sensor (1). The thickness of this layer can be readily selected to minimize oxygen permeation while maximizing the response of the hydrogen gas sensor (1) to atomic hydrogen. The protective molecular diffusion barrier (3) can comprise at least one thin metal film such as palladium, platinum, Iridium, or other noble metals or precursors of such metals that may be used for deposition, or can comprise a polymer such as: polyamides, polyacrylamides, polyacrylate, polyalkylacrylates, polystyrenes, polynitriles, polyvinyls, polyvinylchlorides, polyvinyl alchohols, polydienes, polyesters, polycarbonates, polysiloxanes, polyurethanes, polyolefins, polyimides, or heteropolymeric combinations thereof. See also U.S. Patent Publication No. 20010012539, hereby incorporated by reference herein. The molecular diffusion barrier (3) can be coupled to the catalyst material, or in those embodiments of the invention that do not employ a catalyst layer, can be coupled to the hydrogen gas sensor (1).

Figure 2:
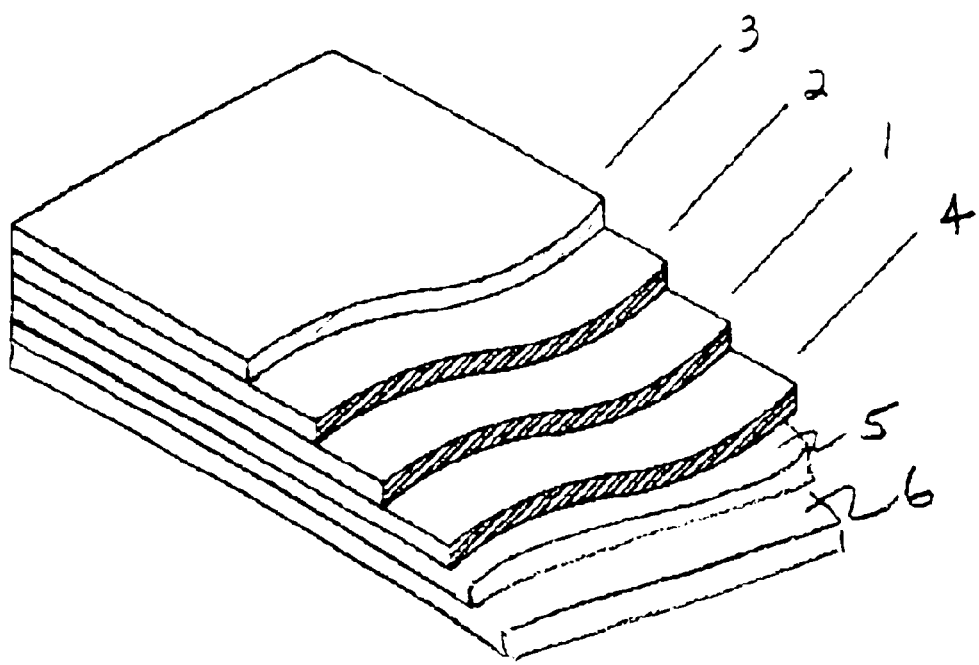
FIG. 2 shows an embodiment of a hydrogen gas sensor having a hydrogen gas sensor material, a catalyst material, and a molecular diffusion barrier selectably permeable to hydrogen gas supported by a substrate material and having a separable or peelable disposable material.

Now referring primarily to FIG. 2, the invention can further comprise a substrate material (4) that supports the hydrogen gas indicator. The substrate material (4) with respect to some embodiments of the invention can be selected from the group of glass, metal, mineral, plastic, paper, or the like. The substrate material (4) can be configured as blanks cut from substantially rigid sheet material; or the substrate material (4) can be a flexibly conformable material that can conformably mate with other objects that carry, interact with, or are employed in the distribution of hydrogen gas, such as pipes, containers, pumps, or the like; or the substrate material (4) can be rigidly configured material that makes up a component or element that is assembled as part of a construct to carry, interact with, or is employed in the distribution of hydrogen gas; or the substrate material (4) can be a material installed to or used within an enclosed area in which hydrogen gas can collect; or the substrate material (4) can be a material used to make clothing, outerwear, or accessories worn by individuals that work or utilize spaces, areas, or enclosures that can potentially bring them into contact with hydrogen gas; or the substrate material can be configured to fit into a container, holder, sampler, badge, or other construct in manner that the hydrogen gas indicator can interact with the gaseous environment.

In some embodiments of the invention the substrate material (4) can further comprise an adhesive layer (5) on at least a portion of the surface of the substrate material (4), such that the substrate material acts, as but one example, similar to adhesive tape. The invention may also further comprise a disposable material (6) to which the substrate material (4) having an adhesive layer (5) on at least a portion of the surface can be separably or peelably joined, such as decals, adhesive strips, adhesive dots, or the like.

In some embodiments of the invention the substrate material (4) can be a friable substrate that can be crumbled or broken into particles. The friable substrate can be made to support the hydrogen sensor indicator prior to being crumbled or broken into particles such that only a portion of the surface of the particle supports a hydrogen gas sensor indicator or can be made to support the hydrogen gas indicator after it is crumbled, broken, or reduced in size to particles such that all the surfaces of the resulting particles support the hydrogen gas sensor indicator. Naturally, the particles may also be made from other types of materials or result from different processes (such as machining, molding, or the like) and comprise numerous particle sizes, types, or kinds in homogeneous populations or mixtures thereof.

In certain embodiments of the invention, the particles that support the hydrogen gas sensor (1) material may be sized to be used as pigments within liquid substances, such as paint, polymers, elastomers, gels, or the like.

Now referring primarily to FIGS. 3, 4, 5, and 6, the invention can further comprise discrete indicia (7) operably responsive to the hydrogen gas sensor (1). As such, the indicia are operably coupled to the hydrogen gas sensor material but provide indication of detection of hydrogen gas in manner that is discrete from the change in physical, chemical, or electrical properties of the hydrogen gas sensor (1) material itself. With respect to some embodiments of the invention, discrete indicia (7) can include alpha-numeric characters or symbols arranged in any number, variety or combination of languages or notations. The alpha-numeric indicia or symbols while operably responsive to the hydrogen gas indicator provide additional indicia discrete from any information that can be obtained directly from the hydrogen sensor indicator itself. The alpha-numeric indicia can, as examples, provide a warning, or could provide instructions, or could provide a map, or display, present, or provide any other information, instruction, or guidance, in response to the presence of hydrogen gas.

Figure 3:
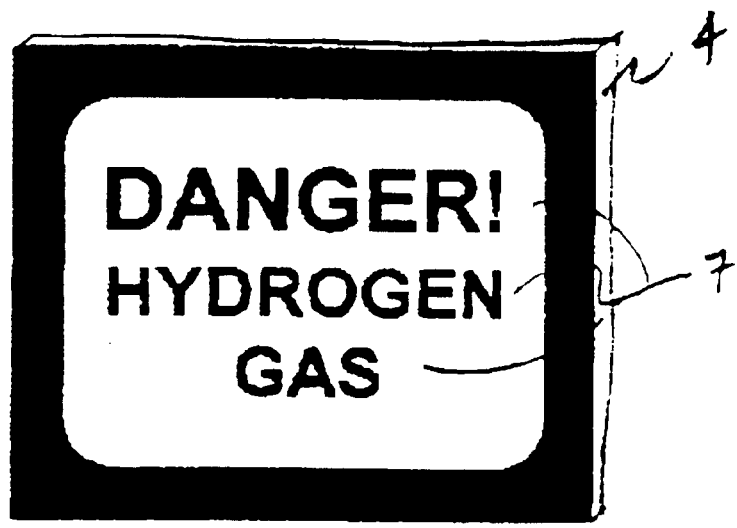
FIG. 3 shows an embodiment of the invention having discrete indicia operably responsive to the hydrogen gas sensor.
Figure 3:
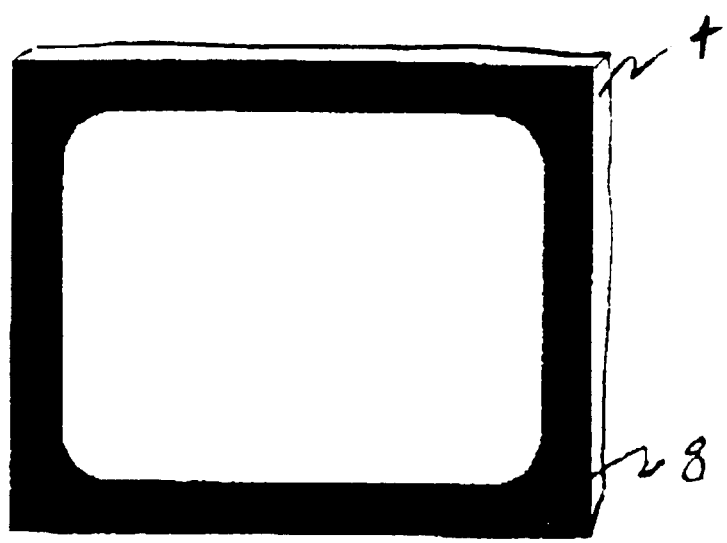

The following illustrative examples of discrete indicia (7) are not meant to limit the numerous and varied embodiments of discrete indicia that can be made operably responsive to the hydrogen gas sensor. As shown by FIG. 3, certain embodiments of the invention can comprise a substrate material (4) having an optical transmission material (8) coupled to portion of the substrate material (4) surface. The optical transmission material (8) could comprise ink, paint, dye, or other pigmented material, but could also be a texture added to the substrate material (4) surface during molding or configuration of the substrate material (4), or could be the result of other treatment of the substrate material (4) surface, such as, particle blasting, surface abrasion, electroplating, chemical vapor deposition, or the like. Discrete indicia of the presence of hydrogen gas are then added such as the words "Danger! Hydrogen Gas" that are operably responsive to the hydrogen gas sensor (1) so that this discrete indicia (7) is provided only in response to the presence of hydrogen gas is present. As indicated above this information could be variety of discrete indicia as desired.

In certain embodiments of the invention, a portion of the substrate material (4) surface can be masked or protected leaving unmasked or unprotected surface configured as discrete indicia (7). The substrate can then be processed by the various methods described above to couple hydrogen gas sensor (1) to the unmasked portion of the substrate material (4) generating discrete indicia (7) that are observable when the hydrogen gas sensor (1) is exposed to hydrogen gas.

In other embodiments of the invention the discrete indicia (7) can be applied as a dye, ink, paint, gel, polymer, or other substance that can entrain hydrogen gas sensor (1) pigment particles (such particles can in some embodiments of the invention also include the catalyst material (2) or the molecular diffusion barrier selectively permeable to hydrogen gas (3) or both as homogeneous populations of particles or in various combinations or permutations). The color or opacity of the substance entraining the hydrogen gas sensor (1) particles applied as discrete indicia (7) could change from a first color or opacity to a second color or opacity in the presence of hydrogen gas.

Figure 4:
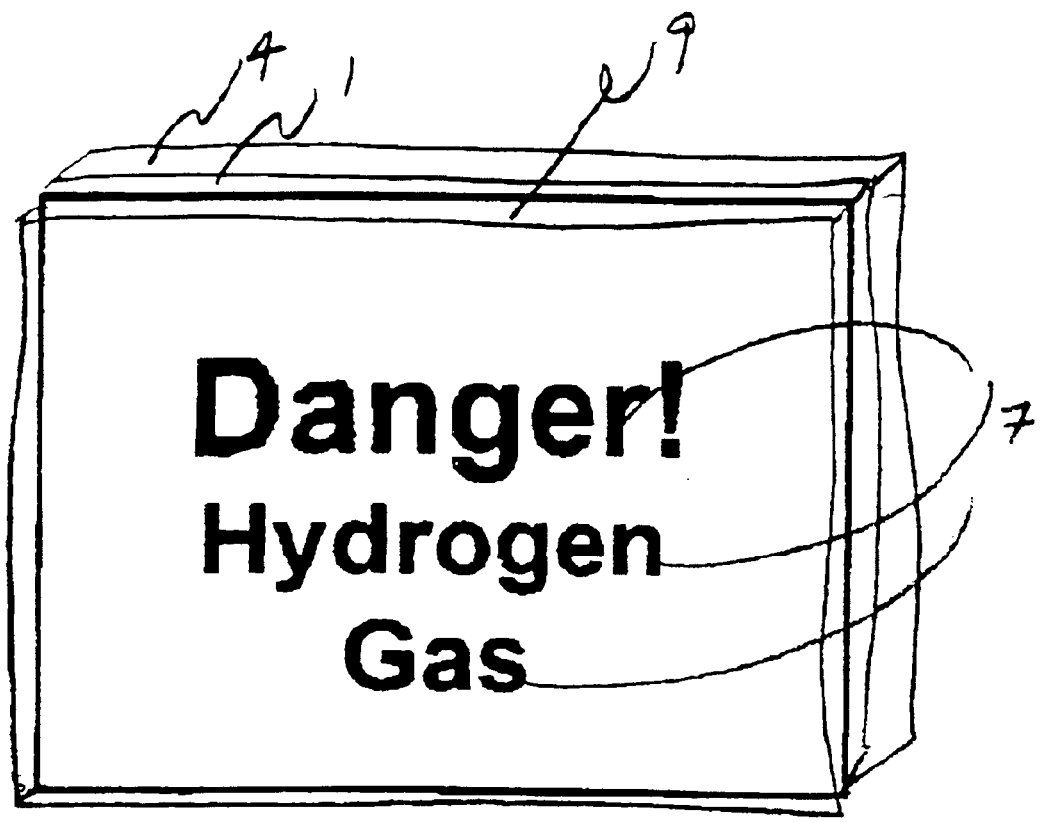
FIG. 4 shows an embodiment of the invention having a layer of hydrogen impermeable material into which discrete indicia are configured.

Now referring primarily to FIG. 4, conventional optical transmission material (8) does not have to be incorporated into all embodiments of the invention. In certain embodiments of the invention a portion of the substrate material (4) surface, as desired, can be coupled to the hydrogen gas sensor (1), and a further hydrogen impermeable material (9) can be coupled to selected portions of the hydrogen gas sensor (which can in some embodiments of the invention also include the catalyst material (2) or the molecular diffusion barrier selectively permeable to hydrogen gas (3) or both) leaving discrete indicia (7) configured in the hydrogen impermeable material (9). When the substrate material (4) is then exposed to hydrogen gas that portion of the hydrogen gas sensor (1) not covered by impermeable material (9) configured with discrete indicia (7) reacts with the hydrogen gas providing viewable discrete indicia (7). Upon removal from hydrogen gas, the hydrogen gas sensor (1) can return to the oxidized color of the transition metal to match the color of the hydrogen gas sensor (1) covered by the hydrogen gas impermeable material (9) and the discrete indicia (7) become substantially undiscernibly.

Figure 5:
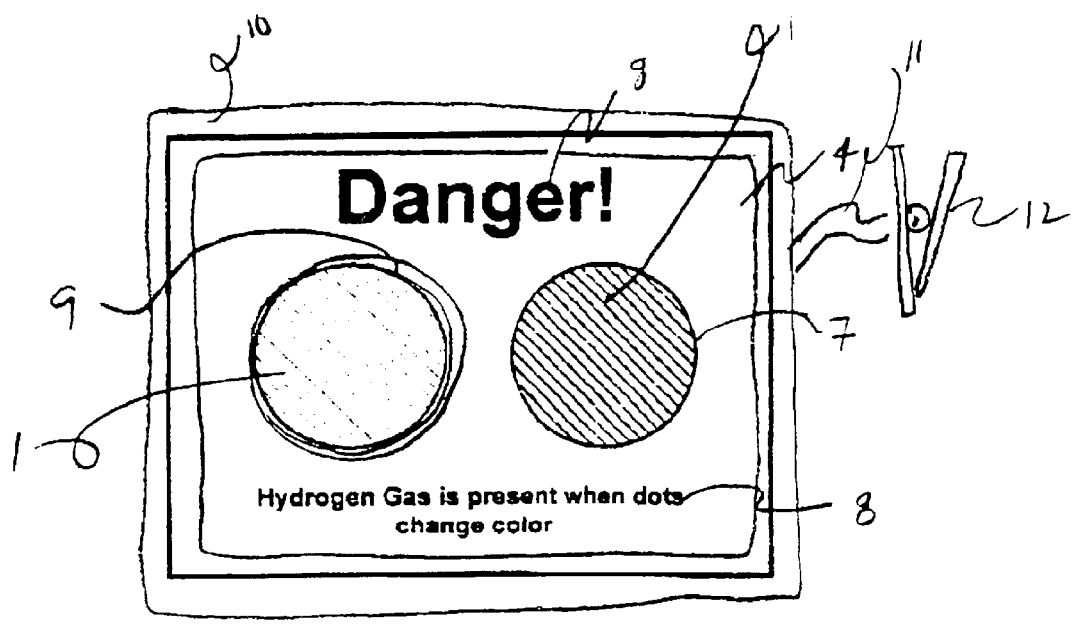
FIG. 5 shows an embodiment of the invention having a substrate material containment element and further including a tether element and a fastener element.

Now referring primarily to FIG. 5, the various embodiments of invention can further include permutations and combinations of the substrate material (4), the hydrogen gas sensor (1) (further including the catalyst material (2) or the molecular diffusion barrier selectively permeable to hydrogen gas (3) or both as desired), the hydrogen impermeable material (9) and conventional optical transmission material (s) (8) as desired. The invention can further comprise a substrate material containment element (10). As shown in FIG. 5, the substrate material containment element can be configured to hold the substrate material (4) in a badge or accessory to be worn on clothing. In certain embodiments, a tether element (11) can be joined to the containment element terminating in a fastener element (12) which can include pins, clips, clasps, adhesive, or the like. In certain embodiments of the invention, the tether element (11) can be attached directly to the substrate material (4). In other embodiments of the invention, the substrate material can be a substrate material (4) conformable to outerwear, such as plastic sheet or paper sheet, having an adhesive layer (5) coupled to at least a portion of the conformable substrate material (4). As to these embodiments, a person can simply press the adhesive layer to outerwear and as to some embodiments of the invention peel the substrate material (4) from the outerwear for disposal, if desired. As described above, the adhesive layer (5) could be separably or peelably joined to a disposable material (6) for convenience of storage, or the convenience of manufacture where a large quantity of a particular substrate material (4) with particular discrete indicia (7) are to be made.

The containment element (10) could also be a container in which hydrogen gas sensor particles are transferred to. The hydrogen gas sensor (1) particles could have a mixture of gases passed over or through them as a manner of sampling the gaseous environment. The containment element holding the hydrogen gas sensor (1) particles could be at a location remote from the gaseous mixture being sampled. The gaseous mixture being sampled transferred to the hydrogen gas indicator by way of a closed conduit communicating between the gaseous mixture and the containment element.

Figure 6:
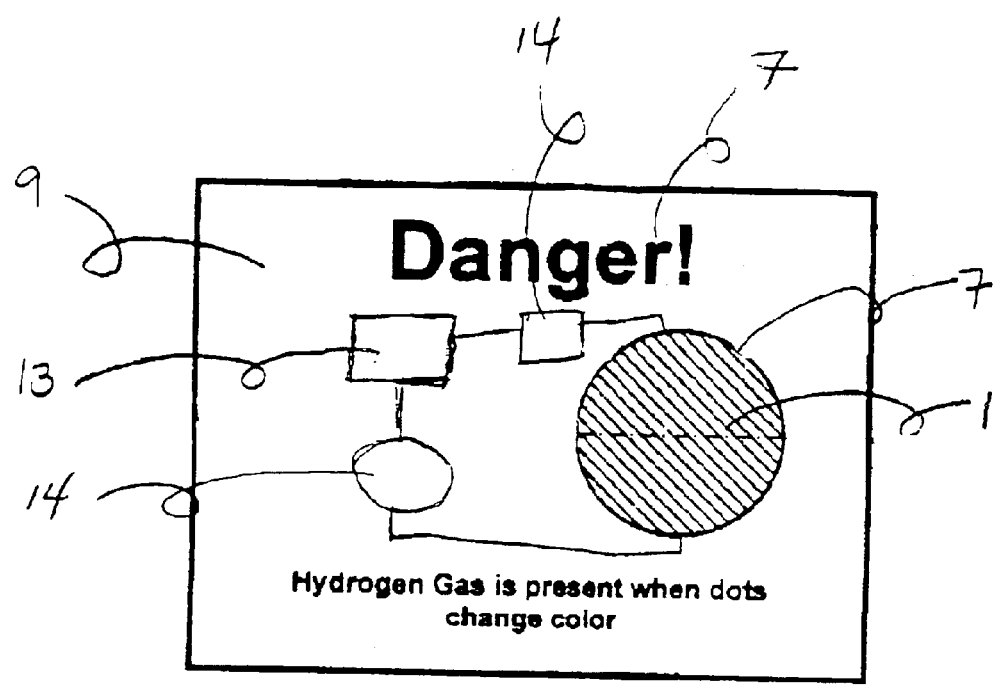
FIG. 6 shows an embodiment of the invention having a circuit operably responsive to the hydrogen sensor element with switchably operable discrete indicia.

Now referring primarily to FIG. 6, embodiments of the invention can further include circuitry that utilizes the reversible electrical properties of the hydrogen gas sensor (1) material (embodiments of the invention can further include the catalyst material (2) or the molecular diffusion barrier (3) selectively permeable to hydrogen gas or both, as desired) as a manner of switching certain discrete indicia (13) on or off in the embodiment of the invention shown by FIG. 6, a power source (14), which could be a battery, photovoltaic cell, or other type of power source provides current, while the hydrogen gas sensor (1) provides a variable resistance or conductance in response to exposure to hydrogen gas. A resistance or conductance differentiation element (14) can be further added to the circuitry as required or desired. When the hydrogen gas sensor (1) is exposed to hydrogen gas the resistance or conductance of the hydrogen gas sensor (1) changes. This change is used to make the switchably operable discrete idicia (13) on or off. Switchably operable discrete indica can include a signal generator that provides a visual or audible or tactile signal. In certain embodiments of the audible signal generator a digitized message can be recited, or a tone generated. In certain embodiments of the tactile signal generator a vibration or modulated frequency is generated that can be felt by a person in proximity to the invention. In certain embodiments of the visual generator an illumination source can be switched on.

As can be easily understood from the foregoing, the basic concepts of the present invention may be embodied in a variety of ways. It involves various embodiments of hydrogen gas sensors and discrete indicia operably responsive to such hydrogen gas sensor(s). In this patent application, the methods and techniques used with hydrogen gas sensors are disclosed as part of the results shown to be achieved by the various devices described and as steps which are inherent to utilization. They are simply the natural result of utilizing the devices as intended and described. In addition, while some devices are disclosed, it should be understood that these not only accomplish certain methods but also can be varied in a number of ways. Importantly, as to all of the foregoing, all of these facets should be understood to be encompassed by this disclosure.

The discussion included in this international Patent Cooperation Treaty patent application is intended to serve as a basic description. The reader should be aware that the specific discussion may not explicitly describe all embodiments possible; many alternatives are implicit. It also may not fully explain the generic nature of the invention and may not explicitly show how each feature or element can actually be representative of a broader function or of a great variety of alternative or equivalent elements. Again, these are implicitly included in this disclosure. Where the invention is described in functionally-oriented terminology, each aspect of the function is accomplished by a device, subroutine, or program. Apparatus claims may not only be included for the devices described, but also method or process claims may be included to address the functions the invention and each element performs. Neither the description nor the terminology is intended to limit the scope of the claims.

Further, each of the various elements of the invention and claims may also be achieved in a variety of manners. This disclosure should be understood to encompass each such variation, be it a variation of an embodiment of any apparatus embodiment, a method or process embodiment, or even merely a variation of any element of these. Particularly, it should be understood that as the disclosure relates to elements of the invention, the words for each element may be expressed by equivalent apparatus terms or method terms—even if only the function or result is the same. Such equivalent, broader, or even more generic terms should be considered to be encompassed in the description of each element or action. Such terms can be substituted where desired to make explicit the implicitly broad coverage to which this invention is entitled. As but one example, it should be understood that all actions may be expressed as a means for taking that action or as an element which causes that action. Similarly, each physical element disclosed should be understood to encompass a disclosure of the action which that physical element facilitates. Regarding this last aspect, as but one example, the disclosure of a "sensor" should be understood to encompass disclosure of the act of "sensing"—whether explicitly discussed or not— and, conversely, were there only disclosure of the act of "sensing", such a disclosure should be understood to encompass disclosure of a "sensor" and even a "means for sensing". Such changes and alternative terms are to be understood to be explicitly included in the description.

Additionally, the various combinations and permutations of all elements or applications can be created and presented. All can be done to optimize the design or performance in a specific application.

Any acts of law, statutes, regulations, or rules mentioned in this application for patent: or patents, publications, or other references mentioned in this application for patent are hereby incorporated by reference. Specifically, U.S. Provisional Patent Application No. 60/251,297, filed Dec. 5, 2000, is hereby incorporated by reference including any figures or attachments, and each of references in the following table of references are hereby incorporated by reference.

US and Foreign Patent Documents

| DOCUMENT NO. | DATE | NAME | CLASS | SUBCLASS | FILING DATE |
| --- | --- | --- | --- | --- | --- |
| 823,734 | Aug. 9, 2001 | Barnard, et al. | 427 | 58 | Mar. 30, 2001 |
| 6,265,222 B1 | Jul. 24, 2001 | DiMeo, Jr. et al. | 436 | 144 | Jan. 15, 1999 |
| 6,277,589 B1 | Aug. 21, 2001 | Seibert et al. | 435 | 30 | May 21, 1999 |
| 6,006,582 | Dec. 28, 1999 | Bhandari et al. | 73 | 23.2 | Mar. 17, 1998 |
| 03318738 | Sep. 25, 1991 | | | | |

Other Documents

Through a mirror, reversibly, Science Update, Nature News Service/Macmilian Magazine, webpage, December 2001, two total pages.

In addition, as to each term used it should be understood that unless its utilization in this application is inconsistent with such interpretation, common dictionary definitions should be understood as incorporated for each term and all definitions, alternative terms, and synonyms such as contained in the Random House Webster's Unabridged Dictionary, second edition are hereby incorporated by reference. However, as to each of the above, to the extent that such information or statements incorporated by reference might be considered inconsistent with the patenting of this/these invention(s) such statements are expressly not to be considered as made by the applicant(s).

In addition, unless the context requires otherwise, it should be understood that the term "comprise" or variations such as "comprises" or "comprising", are intended to imply the inclusion of a stated element or step or group of elements or steps but not the exclusion of any other element or step or group of elements or steps. Such terms should be interpreted in their most expansive form so as to afford the applicant the broadest coverage legally permissible in countries such as Australia and the like.

Thus, the applicant(s) should be understood to have support to claim at least: i) each of the hydrogen gas sensors and discrete indicia as herein disclosed and described, ii) the related methods disclosed and described, iii) similar, equivalent, and even implicit variations of each of these devices and methods, iv) those alternative designs which accomplish each of the functions shown as are disclosed and described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, and x) the various combinations and permutations of each of the elements disclosed.

The claims set forth in this specification are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the subject matter for which protection is sought by this application or by any subsequent continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

I claim:

1. A hydrogen gas indicator, comprising:
   a. a substrate material;
   b. an atomic hydrogen gas sensor supported by said substrate material wherein said atomic hydrogen gas sensor is selected from the group consisting of vanadium oxide, tungsten oxide, molybdenum oxide, yttriun oxide, and combinations thereof;
   c. a catalyst material coupled to said atomic hydrogen gas sensor, wherein said catalyst material converts molecular hydrogen gas to atomic hydrogen gas sensed by said atomic hydrogen gas sensor;
   d. a gas diffusion barrier coupled to said catalyst material wherein said gas diffusion barrier is selectively permeable to molecular hydrogen gas; and
   e. discrete indicia operably responsive to said atomic hydrogen gas sensor.

2. A hydrogen gas indicator as described in claim 1, wherein said substrate material comprises a friable substrate material.

3. A hydrogen gas indicator as described in claim 1, wherein said catalyst material is selected from the group consisting of platinum, palladium, rhodium, nickel, and alloys of these materials with other metals.

4. A hydrogen gas indicator as described in claim 1, wherein said substrate material comprises a particulate material.

5. A hydrogen gas indicator as described in claim 1, wherein said particulate material comprises particles used as pigments.

6. A hydrogen gas indicator as described in claim 1, wherein said discrete indicia operably responsive to said atomic hydrogen gas sensor comprises symbols or characters applied to a surface using a liquid substance containing said particles used as pigments.

7. A hydrogen gas indicator as described in claim 4, further comprising a containment element at least partially filled with said particulate material.

8. A hydrogen gas indicator as described in claim 1, wherein said substrate material further comprises:
   i. at least a portion of a first surface having an adhesive layer; and
   ii. at least at least a portion of a second surface that supports said hydrogen gas sensor.

9. A hydrogen gas indicator as described in claim 1, wherein said substrate material further comprises:
   i. at least one surface separably joined to a disposable material; and
   ii. at least One surface that supports said hydrogen gas sensor.

10. A hydrogen gas indicator as described in claim 9, further comprising an adhesive layer coupled to at least a portion of said at least one surface separably joined to said disposable material.

11. A hydrogen gas indicator as described in claim 10, wherein said adhesive layer becomes operable upon separation of said at least one surface separably joined to said disposable material.

12. A hydrogen gas indicator as described in claim 1, further comprising a holder element coupled to said substrate material.

13. A hydrogen gas indicator as described in claim 12, further comprising at least one fastener element coupled to said holder element.

14. A hydrogen gas indicator as described in claim 1, wherein said discrete indicia element are selected from the group consisting of symbols and alphabet characters.

15. A hydrogen gas indicator, comprising:
   a. a friable substrate material;
   b. an atomic hydrogen gas sensor supported by said friable substrate material wherein said atomic hydrogen gas sensor is selected from the group consisting of vanadium oxide, tungsten oxide, molybdenum oxide, yttrium oxide, and combinations thereof;
   c. a catalyst material coupled to said atomic hydrogen gas sensor which converts molecular hydrogen gas to said atomic hydrogen gas sensed by said atomic hydrogen gas sensor; and
   d. a gas diffusion barrier coupled to said catalyst material, wherein said gas diffusion barrier is selectively permeable to molecular hydrogen gas.

16. A hydrogen gas indicator as described in claim 15, wherein said catalyst material is selected from the group consisting of platinum, palladium, rhodium, nickel, and alloys of these materials with other metals.

17. A hydrogen gas indicator as described in claim 15, wherein said friable substrate material comprises particulate material used as pigments.

18. A hydrogen gas indicator as described in claim 16, further comprising discrete indicia operably responsive to said atomic hydrogen gas sensor.

19. A hydrogen gas indicator as described in claim 18, wherein said discrete indicia operably responsive to said atomic hydrogen gas sensor comprises symbols or characters applied to a surface using a liquid substance containing said particles used as pigments.

20. A hydrogen gas indicator as described in claim 15, further comprising a containment element at least partially filled with particulate material generated from said friable material.

21. A hydrogen gas indicator as described in claim 20, further comprising a holder element coupled to said containment element.

22. A hydrogen gas indicator as described in claim 21, further comprising at least one fastener element coupled to said holder clement.

23. A hydrogen gas indicator, comprising:
   a. a substrate material;
   b. an atomic hydrogen gas sensor supported by said substrate material, wherein said atomic hydrogen gas sensor reversibly switches from a first conduction state to a second conduction state in response to atomic hydrogen gas and wherein said atomic hydrogen gas sensor is selected from the group consisting of vanadium oxide, tungsten oxide, molybdenum oxide, yttrium oxide, and combinations thereof;
   c. a catalyst material that facilitates conversion of molecular hydrogen gas to said atomic hydrogen gas;
   d. a gas diffusion barrier coupled to said catalyst material, wherein said gas diffusion barrier is selectively permeable to molecular hydrogen gas;
   e. a circuit operably responsive to said atomic hydrogen gas sensor; and
   f. at least one discrete indicia element responsive to said circuit.

24. A method of indicating hydrogen gas, comprising the steps of:
   a. providing a hydrogen gas indicator, wherein said hydrogen gas indicator comprises:
      i. a substrate material;
      ii. an atomic hydrogen gas sensor supported by said substrate material wherein said atomic hydrogen gas sensor is selected from the group consisting of vanadium oxide, tungsten oxide, molybdenum oxide, yttrium oxide, and combinations thereof;
      iii. a catalyst material coupled to said atomic hydrogen gas sensor, wherein said catalyst material converts molecular hydrogen to atomic hydrogen gas sensed by said atomic hydrogen gas sensor;
      iv. a gas diffusion barrier coupled to said catalyst material, wherein said gas diffusion barrier is selectively permeable to said molecular hydrogen gas;
   b. detecting said molecular hydrogen gas with said hydrogen gas indicator; and
   c. indicating detection of said molecular hydrogen gas with discrete indicia operably coupled to said atomic hydrogen gas sensor.

25. A method of indicating hydrogen gas as described in claim 24, further comprising the step of generating hydrogen gas indicator particles.

26. A method of indicating hydrogen gas as described in claim 25, wherein said step of generating hydrogen gas indicator particles comprises establishing hydrogen gas indicator particles having a size suitable as pigments within a liquid substance.

27. A method of indicating hydrogen gas as described in claim 24, wherein said step of indicating detection of said molecular hydrogen gas with discrete indicia operably coupled to said atomic hydrogen gas sensor comprises applying symbols or characters to a surface of a second substrate material using said liquid substance containing said hydrogen gas indicator particles having a size suitable as pigments.

28. A method of indicating hydrogen gas as described in claim 24, further comprising the step of establishing an adhesive layer on a portion of said surface of said second substrate material.

29. A method of indicating hydrogen gas as described in claim 28, further comprising the step of separably joining said adhesive layer on said portion of said surface of said second substrate material to a disposable substrate material.

30. A method of indicating hydrogen gas as described in claim 29, further comprising the steps of:
   a. separating said adhesive layer on said portion of said surface of said second substrate material from said disposable substrate material;
   b. maintaining said adhesive layer on said portion of said surface of said second substrate material; and
   c. adhering said second substrate material to a surface location with said adhesive layer.

31. A method of indicating hydrogen gas as described in claim 25, further comprising the step of transferring said hydrogen gas indicator particles to a containment element.

32. A method or indicating hydrogen gas as described in claim 31, further comprising the step of passing a volume of a gas through said hydrogen gas indicator particles.

33. A method of indicating hydrogen gas as described in claim 24, further comprising the steps of:
   a. coupling a circuit responsive to said atomic hydrogen gas sensor;
   b. generating an audible sound in response to detection of atomic hydrogen gas by said atomic hydrogen gas sensor.

* * * * *